United States Patent [19]

Ichikawa et al.

[11] Patent Number: 5,797,937
[45] Date of Patent: Aug. 25, 1998

[54] OPHTHALMOLOGIC KNIFE

[75] Inventors: Kazuo Ichikawa, Nagoya; Toshiyuki Nakajima, Tokyo, both of Japan

[73] Assignee: Canon Staar Co. Inc., Tokyo, Japan

[21] Appl. No.: 683,194

[22] Filed: Jul. 18, 1996

[30] Foreign Application Priority Data

Jul. 31, 1995 [JP] Japan .................. 7-195045

[51] Int. Cl.⁶ .................................. A61B 17/32
[52] U.S. Cl. .................. 606/167; 606/131; 606/132
[58] Field of Search ................ 606/166, 167, 606/131, 132, 170; 30/353, 49; 128/754

[56] References Cited

U.S. PATENT DOCUMENTS

| | | | |
|---|---|---|---|
| 1,573,681 | 2/1926 | Daireaux | 606/167 |
| 2,838,049 | 6/1958 | Eidsenhofer et al. | 606/167 |
| 3,798,688 | 3/1974 | Wasson | 30/353 |
| 3,929,138 | 12/1975 | Curi | 606/167 |
| 4,844,070 | 7/1989 | Dee | 606/167 |
| 5,186,178 | 2/1993 | Yeh et al. | 128/754 |
| 5,217,477 | 6/1993 | Lager | 606/166 |
| 5,269,316 | 12/1993 | Spitalny et al. | 606/167 |
| 5,336,235 | 8/1994 | Myers | 606/166 |

*Primary Examiner*—Michael Buiz
*Assistant Examiner*—Nancy Mulcare
*Attorney, Agent, or Firm*—Ladas & Parry

[57] ABSTRACT

An ophthalmologic knife includes a handle, and a blade having a base portion fixed to the tip of the handle and an incision-forming portion integrally formed with the base portion. The entire portion of the blade or at least part of the incision-forming portion which is inserted into the cornea of an eyeball has an arcuate cross section. By using the ophthalmologic knife, a three-dimensional incision having an arcuate cross section is formed in the cornea or the like. When a three-dimensional object having a cylindrical cross section or the like is inserted into the incision, the convex portion surrounded by the incision is bent toward the inside of the eyeball. This allows smooth insertion of the object.

11 Claims, 6 Drawing Sheets

FIG.1
(PRIOR ART)
FIG.2
(PRIOR ART)
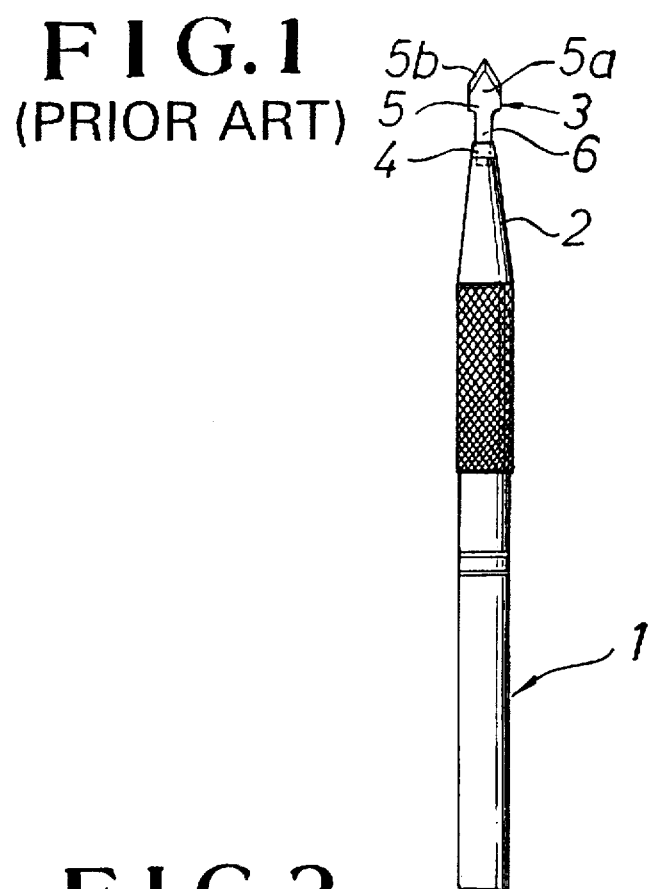
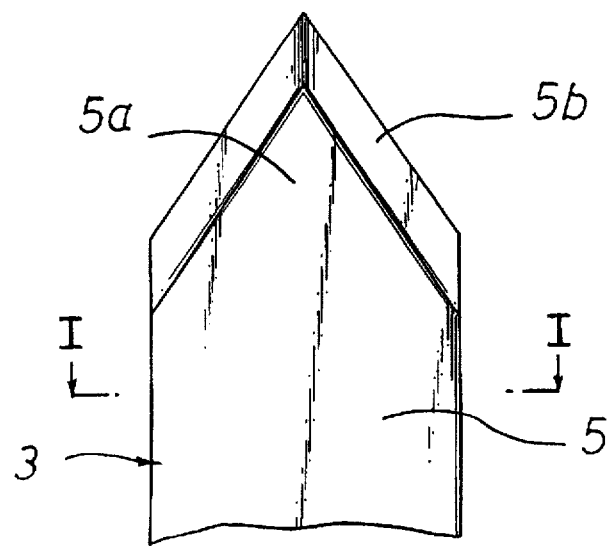

SECTION I-I

SECTION II-II

SECTION III-III

SECTION IV-IV

OPHTHALMOLOGIC KNIFE

BACKGROUND OF THE INVENTION

1. Field of the Invention

The present invention relates to an ophthalmologic knife, and more particularly to an ophthalmologic knife used in ophthalmologic surgery for making a small incision in the eyeball. When ophthalmologic surgery for cataract is performed for extracting an opaqued natural lens because of cataract so as to replace it with an artificial lens, i.e., intraocular lens, a cylindrical ultrasonic chip of an ultrasonic emulsification/suction apparatus is inserted into the eyeball through a small incision so as to crush and emulsify the opaque natural lens and suck it for extraction, and the intraocular lens is inserted in a folded state into the eyeball through the incision. The ophthalmologic knife of the present invention is applicable to such ophthalmologic surgery.

2. Discussion of Related Art

Implantation of an intraocular lens for treating cataract has been widely performed since 1949, when Ridley implanted for the first time an artificial lens, i.e., intraocular lens into the human eye in place of an opaqued natural lens during cataract surgery.

The intraocular lens used first had an optical portion made of polymethyl methacrylate (PMMA). The implantation of the intraocular lens was accompanied by complications which occurred after the cataract surgery. Many ophthalmologists have shown interest in the complications and have studied them. As a result, most of the problems have been solved. However, since the optical portion is made of a hard material, an incision for implantation of such an intraocular lens must have a dimension somewhat greater than the diameter of the optical portion. Therefore, an incision to be formed in the eyeball is large, and therefore the following problems have remained unsolved:

1) necessity of suture of the incision;
2) increase in the degree of astigmatism after surgery due to suture of the incision; and
3) necessity of entering a hospital for a predetermined period so as to enable observation of the postoperative conditions.

A method of surgery has been pointed out as a cause of the above-mentioned complications. That is, the conventional surgery for extracting a natural lens because of cataract has been performed by using an ECCE (extracapsular cataract extraction) operation technique in which a lens is extracted without crushing it. Since this operation technique has required formation of an incision of about 10 mm, the operation caused astigmatism quite often. To solve this problem, a technique called pharmacoemulsification (PEA) using an ultrasonic emulsification/suction apparatus has been developed recently.

In this method, an opaqued natural lens is crushed and emulsified using ultrasonic waves emitted from a cylindrical ultrasonic chip, and is sucked for extraction. When this method is used, the size of an incision formed in the eyeball can be decreased to a size sufficient for insertion of the cylindrical ultrasonic chip. A crushed lens can be extracted through an incision of about 3 to 4 mm. Therefore, this method makes it possible to perform the extraction operation by forming only a small incision, which mitigates the astigmatism after the operation. However, since the optical portion is made of a hard material, an incision for implantation of such an intraocular lens must have a dimension somewhat greater than the diameter of the optical portion, as mentioned above. In the case of a standard intraocular lens having an optical portion of 6.0 mm, an incision having a size equal to or greater than 6.5 mm must be formed. Therefore, even if an opaqued natural lens is extracted through a small incision using pharmacoemulsification, the incision must be widened so as to insert an intraocular lens. Accordingly, the problem of astigmatism occurring after surgery due to the large incision has not been solved.

In order to mitigate astigmatism after surgery, improved intraocular lenses have been developed which can decrease the size of incisions. Examples of such improved lenses include an intraocular lens having an oval optical portion which is inserted into an incision such that its smaller radius is oriented in the direction of the incision, and an intraocular lens with an optical portion having a reduced diameter. However, each of these intraocular lenses still has a hard optical portion. Therefore, employment of these intraocular lenses decreases the incision size only to about 5.5 mm (i.e., only by about 1 mm).

In order to partially solve the above-described problem, an improved operation technique has been developed. As described above, the formation of a large incision causes the problem of formation of a large cut in the tissue of the eyeball which in turn causes astigmatism due to the cut. The formation of a large incision also causes the problem of necessity of suture after surgery to close the incision which in turn causes astigmatism, the degree of which varies depending on the strength of the suture. The former problem has not been solved because the incision must have a sufficient size which allows insertion of an intraocular lens having a hard optical portion. However, the latter problem has been solved by an operation technique in which a self-closing incision consisting of stepped planes is formed. This self-closing incision utilizes the internal pressure of the anterior chamber so as to eliminate the necessity of suture.

In addition to the above-described improvements such as pharmacoemulsification which makes it possible to extract an opaqued natural lens through a small incision, and the method in which no suture is performed after surgery so as to mitigate astigmatism, intraocular lenses themselves have been improved and have come into use recently.

Such an improved intraocular lens is disclosed in Japanese Patent Application No. 58-18005 (Japanese Patent Application Laid-Open (kokai) No. 58-146346). In the intraocular lens, at least an optical portion is made of a deformable elastic material having a predetermined memory characteristic. Alternatively, at least an optical portion is made of an elastic material having a predetermined memory characteristic, and supports are provided which are made of a material different from that of the optical portion and are adapted to support the optical portion within an eye. Moreover, as disclosed in Japanese Patent Application Nos. 58-18005, 3-60188, 3-142067, 3-142068, and 3-143079, improved insertion tools have been proposed. Using these tools, the optical portion of an intraocular lens is compressed, rolled, bent, stretched, or folded so as to reduce its exterior size, thereby making it possible to insert the intraocular lens through a small incision. These intraocular lenses and insertion tools therefor make it possible to perform surgery by forming only a small incision, thereby mitigating astigmatism after surgery.

More recently, a further improved insertion tool has been developed which does not widen an incision for pharmacoemulsification and which allows an intraocular lens to be inserted into an eye through the un-widened incision.

In the above-described progress in the method of cataract surgery and in intraocular lenses, the newest method for cataract surgery is a method for forming a small incision in the cornea. This method not only mitigates astigmatism as in the conventional method so that the view function of a patient after surgery, i.e., the quality of life after surgery is improved, but also provides various advantages such as reduced bleeding, facilitated operation of a tool during surgery, and shortened surgery time. These advantages reduce a burden on a patient, and make it possible to perform one-day operation which does not require the patient to be hospitalized.

In the above-described conventional techniques and methods, a cylindrical chip of an ultrasonic emulsion/suction apparatus, a deformable intraocular lens, a cylindrical nozzle of an insertion tool, or a forceps for holding a folded intraocular lens (hereinafter collectively referred to as a "three-dimensional object") is inserted into a small incision. Further, a tool or the like is operated while being inserted into the incision. However, when the incision is formed using a conventional ophthalmologic knife, the following problems occur.

FIGS. 1–4, show an example of a conventional ophthalmologic knife used for forming an incision. A truncated cone-shaped mounting portion 2 is formed at the tip of an elongated bar-shaped handle 1. The base portion 4 of a blade 3 is inserted into and fixed to the mounting portion 2. A flattened incision-forming portion 5 is extended from the tip portion of the base portion 4. The incision-forming portion 5 has a pointed tip portion 5a, and a cutting surface 5b is formed at each side edge portion located on either side of the tip portion 5a such that the cutting surface 5b is formed on each of the front and back sides of each side edge portion. The incision-forming portion 5 is formed into a generally hexagonal shape (or a pentagonal shape) and is connected integrally to the base portion 4 via a narrow connecting portion 6.

The blade 3 is formed substantially symmetrically with respect to the axis of the handle 1. The cutting surface 5b may be formed on one of the front and back faces.

A surgeon holds the handle 1 in his/her hand and cuts the cornea or the like using the cutting surfaces 5b of the incision-forming portion 5, thereby forming a straight incision 7 as shown in FIG. 5.

When a self-closing incision is formed, a surgeon does not simply insert the incision-forming portion 5 into the cornea or the like. Rather, the surgeon moves the incision-forming portion 5 such that an incision consisting of stepped planes is formed.

However, in both cases, since the incision-forming portion 5 is flat, the shape of the formed incision is also flat. Therefore, when the above-described three-dimensional object having a circular cross section, rectangular cross section or a like cross section is inserted into the incision, the flat small incision formed straightly in the horizontal direction is widened in the vertical direction as illustrated by a dashed line in FIG. 5, so that stresses such as a stretching force act on the incision and the tissue adjacent to the incision, resulting in damage thereof. In the case where a self-closing incision is formed, in addition to the damage of the incision and the tissue adjacent thereto, there occurs the problem that the self-closing incision sometimes does not close by itself. Moreover, in an operation in which a small incision is formed in the cornea so as to shorten the operation time, thereby decreasing the burden on a patient, the damage of the incision and the tissue adjacent thereto becomes larger and effects caused thereby also increase, because the cornea is weaker than the sclera in which an incision has conventionally been formed.

SUMMARY OF THE INVENTION

An object of the present invention is to solve the above-described problems and to provide an improved ophthalmologic knife which can form a three-dimensional incision into an eyeball, which can prevent the incision and the tissue adjacent to the incision from being damaged even when a three-dimensional object is inserted into the incision, and which does not prevent a self-closing incision from closing by itself.

Briefly, the present invention provides an ophthalmologic knife comprising a handle, and a blade having a base portion fixed to the tip of the handle and an incision-forming portion integrally formed with the base portion. The entire portion of the blade or at least part of the incision-forming portion which is inserted into an eyeball has a non-planar cross section.

The non-planar cross section may be an arcuate cross section, an inverted-V-shaped cross section, or the like.

Therefore, when the ophthalmologic knife of the present invention is used, a three-dimensional incision having an arcuate or inverted-V-shaped cross section can be formed in the cornea or sclera of an eyeball. Therefore, when a three-dimensional object is inserted into the incision, a concaved portion located on one side of the incision allows smooth insertion of the object, so that the concaved side is neither distorted nor damaged. Moreover, a convex portion surrounded by the incision is bent toward the inside of the eyeball, so that the incision is not expanded in such a direction that the incision is opened in the vertical direction.

Accordingly, when the ophthalmologic knife of the present invention is used, a three-dimensional incision can be formed, which prevents the incision itself and the tissue adjacent to the incision from being damaged. Although the convex portion is bent toward the inside of an eyeball due to insertion of an object, the convex portion returns its original position due to the internal pressure of the eyeball immediately after the object is withdrawn so that a self-closing incision having an improved closing action can be formed.

Preferably, the portion of the incision-forming portion, which extends from the tip of a cutting surface to a position slightly closer to the base portion relative to the base end of the cutting surface, is used as an insertion portion which is inserted into an eyeball.

In this case, an arcuate or inverted-V-shaped incision having a predetermined shape and dimensions can be formed in the cornea or the like of an eyeball by inserting the insertion portion of the incision-forming portion into the eyeball.

BRIEF DESCRIPTION OF THE ACCOMPANYING DRAWINGS

Various other objects, features and many of the attendant advantages of the present invention will be readily appreciated as the same becomes better understood by reference to the following detailed description of the preferred embodiments when considered in connection with the accompanying drawings, in which:

FIG. 1 is a schematic plan view of a conventional ophthalmologic knife;

FIG. 2 is an enlarged plan view of the blade of the conventional ophthalmologic knife shown in FIG. 1;

DETAILED DESCRIPTION OF THE PREFERRED EMBODIMENTS

Embodiments of the present invention will now be described with reference to the drawings.

Figure 3:
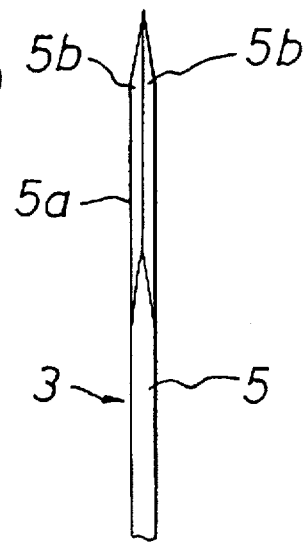
FIG. 3 is an enlarge side view of the blade of the conventional ophthalmologic knife shown in FIG. 1.
Figure 4:
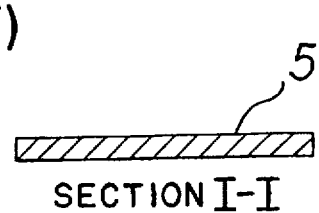
FIG. 4 is a cross section taken along the line I—I in FIG. 2.
Figure 5:
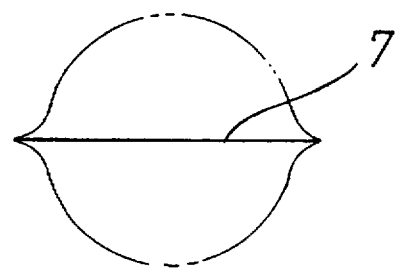
FIG. 5 is a front view of an incision formed using the conventional ophthalmologic knife.
Figure 6:
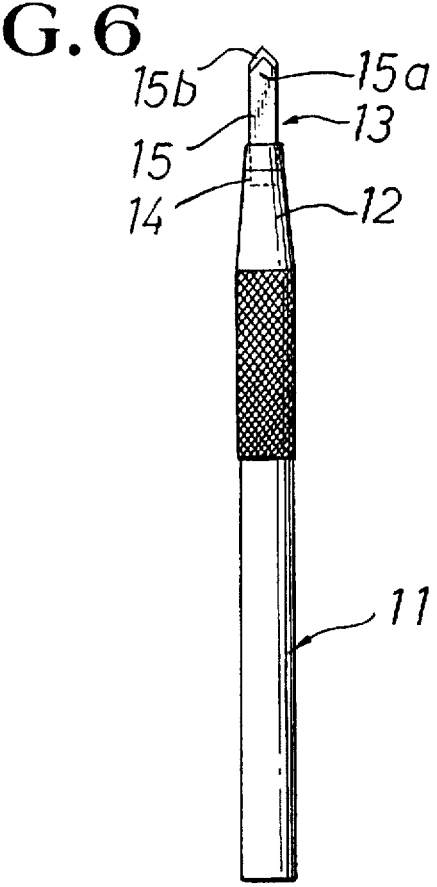
FIG. 6 is a schematic plan view of an ophthalmologic knife according to a first embodiment of the present invention.
Figure 7:
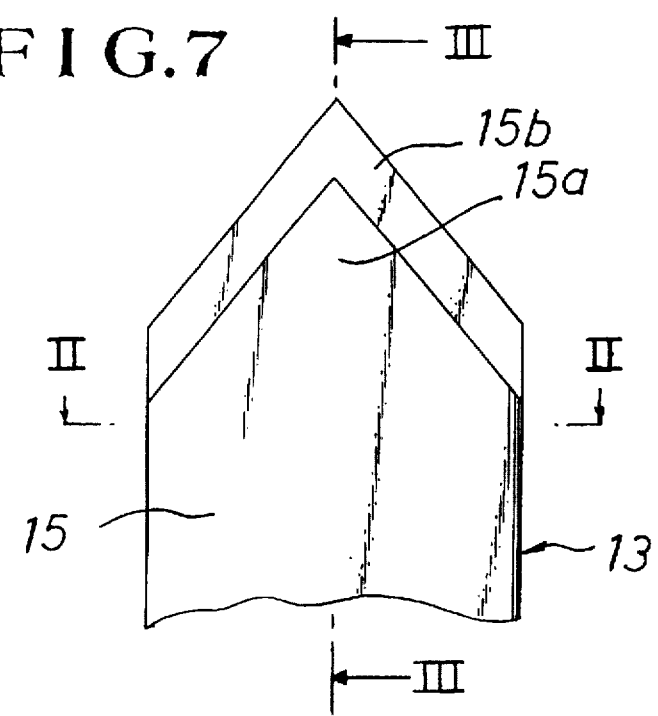
FIG. 7 is an enlarged plan view of the blade of the ophthalmologic knife shown in FIG. 6.
Figure 8:
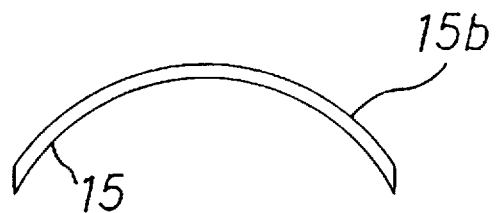
FIG. 8 is an enlarged front view of the blade of the ophthalmologic knife shown in FIG. 6.
Figure 9:
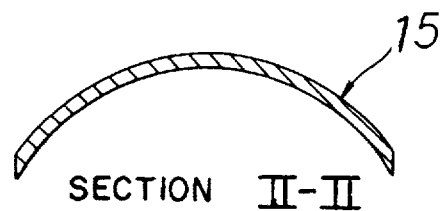
FIG. 9 is a cross section taken along the line II—II in FIG. 7.

FIGS. 6–9 show an ophthalmologic knife according to a first embodiment of the present invention, wherein FIG. 6 is a schematic plan view of the ophthalmologic knife, FIG. 7 is an enlarged plan view of the blade of the ophthalmologic knife, FIG. 8 is an enlarged front view of the blade of the ophthalmologic knife, and FIG. 9 is a cross section taken along the line II—II in FIG. 7.

The ophthalmologic knife according to the first embodiment has an elongated bar-shaped handle 11, and a truncated cone-shaped mounting portion 12 is formed at the tip of the handle 11. The base portion 14 of a blade 13 is inserted into and fixed to the mounting portion 12. A incision-forming portion 15 is extended from the base portion 14 such that the tip portion of the base portion 14 and the incision forming portion 15 axially project from the tip of the handle 11.

Figure 10:
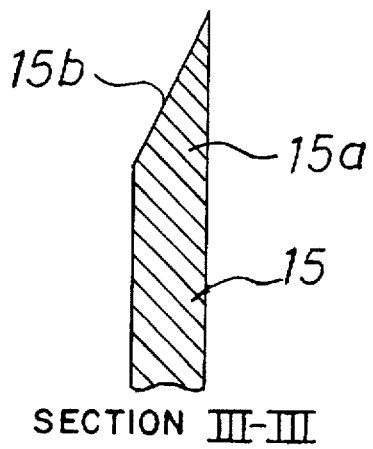
FIG. 10 is a longitudinal cross section of the blade of the ophthalmologic knife shown in FIG. 6 taken along the line III—III.

The blade 13 has a width in a direction perpendicular to the axis of the handle 11 and is curved upwardly as shown in FIG. 8, so that the blade 13 has an arcuate cross section over the entire length. The incision-forming portion 15 has a pointed tip portion 15a, and a cutting surface 15b is formed on each side edge portion located on either side of the pointed tip of the tip portion 15a such that the cutting surface 15b is formed only on the front side of each side edge portion, as shown in FIG. 10.

Figure 11:
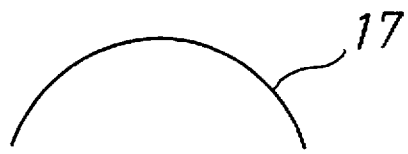
FIG. 11 is a front view of an incision formed using the ophthalmologic knife of the first embodiment.

When a surgeon uses the ophthalmologic knife according to the first embodiment, the incision-forming portion 15 is cut into the cornea of an eyeball, so that a three-dimensional incision 17 having an arcuate cross section is formed as shown in FIG. 11. At this time, it is preferable that an insertion portion extending from the tip of the incision-forming portion 15 to the line II—II in FIG. 7 (i.e., from the tip of the cutting surface 15b to a point slightly closer to the base portion relative to the base end of the cutting surface 15b) be inserted into the eyeball.

Figure 12:
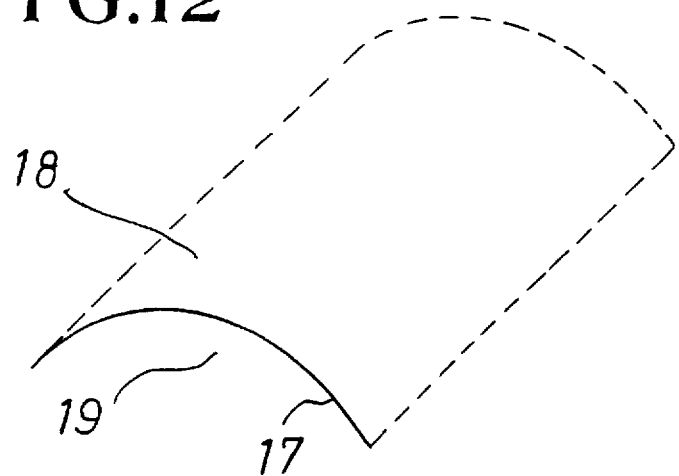
FIG. 12 is an explanatory diagram showing the movement of the knife for forming the incision shown in FIG. 11.

Subsequently, a three-dimensional object such as an ultrasonic chip of an ultrasonic emulsification/suction apparatus is inserted into the arcuate incision 17. As shown in FIG. 12, when the three-dimensional object is inserted into the incision 17, a concaved portion 18 located on the upper side of the incision 17 allows smooth insertion of the object, so that the concaved portion 18 is neither distorted nor damaged. Moreover, a convex portion 19 located on the lower side of the incision 17 is bent toward the inside of the eyeball, so that the incision is not expanded in such a direction that the incision is opened in the vertical direction. The convex portion 19 on the lower side returns its original position due to the internal pressure of the eyeball immediately after the object is withdrawn, so that the incision 17 has an improved closing action compared to an incision formed using a conventional knife.

Figure 13A:
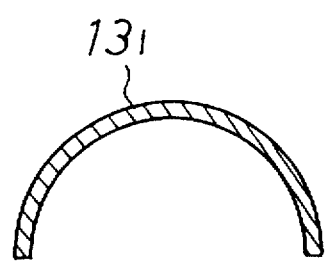
FIGS. 13A, 13B and 13C are enlarged transversal cross sections of blades, each of which shows a modification of the ophthalmologic knife of the first embodiment.
Figure 13B:
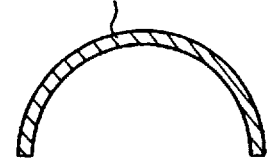
Figure 13C:

FIGS. 13A, 13B and 13C are enlarged transversal cross sections of blades, each of which shows a modification of the ophthalmologic knife of the first embodiment. Numerals 131, 132 and 133 denote blades having arcuate cross sections whose curvatures differ from that of the blade according to the first embodiment. Except the blade, these ophthalmologic knifes have the same structure as that of the ophthalmologic knife according to the first embodiment.

The ophthalmologic knifes according to the modifications are selectively used in accordance with the size and shape of a three-dimensional object to be inserted. That is, an ophthalmologic knife having a curvature suitable for an object to be inserted is used, whereby effects similar to those provided by the first embodiment can be obtained.

Figure 14:
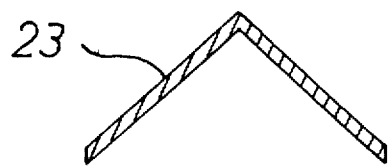
FIG. 14 is an enlarged transversal cross section of a blade of an ophthalmologic knife according to a second embodiment of the present invention.

FIG. 14 is an enlarged transversal cross section of a blade of an ophthalmologic knife according to a second embodiment of the present invention. Numeral 23 denotes a blade having an inverted-V-shaped cross section. Except the blade, this ophthalmologic knife has the same structure as that of the ophthalmologic knife according to the first embodiment.

The ophthalmologic knife according to the second embodiment can be used to form a three-dimensional incision having an inverted-V-shaped cross section in the cornea or the like. This ophthalmologic knife also provides effects similar to those provided by the first embodiment.

Figure 15:
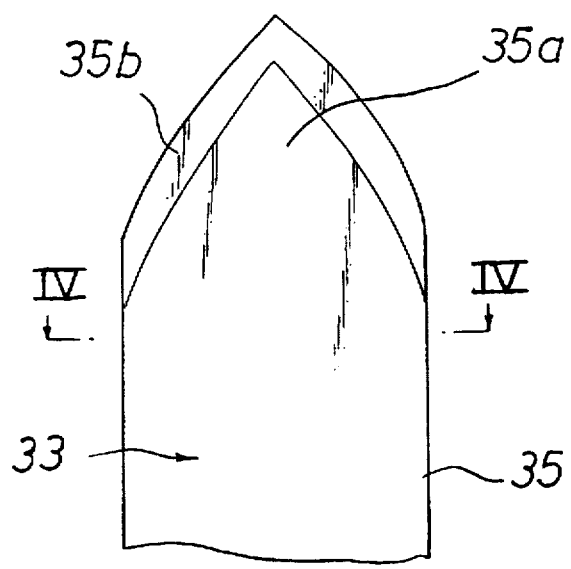
FIG. 15 is an enlarged plan view of a blade of an ophthalmologic knife according to a third embodiment of the present invention.
Figure 16:
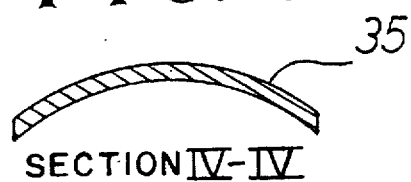
FIG. 16 is a cross section taken along the line IV—IV in FIG. 15.

FIG. 15 is an enlarged plan view of a blade of an ophthalmologic knife according to a third embodiment of the present invention, and FIG. 16 is a cross section taken along the line IV—IV in FIG. 15. Numeral 35 denotes an incision-forming portion of a blade 33. The tip portion 35a of the incision-forming portion 35 is pointed, and both side edges are slightly extended outwardly such that each side edge has a curved shape. A cutting surface 35a is formed on each side edge such that the cutting surface 35a has a substantially constant width. The arcuate cross section of the blade 33 has a curvature smaller than that of the first embodiment. Except the blade, this ophthalmologic knife has the same structure as that of the ophthalmologic knife according to the first embodiment.

The ophthalmologic knife according to the third embodiment has a cross section different from that of the first embodiment. Therefore, an incision having a different cross section can be formed in the cornea or the like. By selectively using this knife in accordance with the portion in which an incision to be formed and in accordance with other factors, effects similar to those provided by the first embodiment can be obtained.

Figure 17:
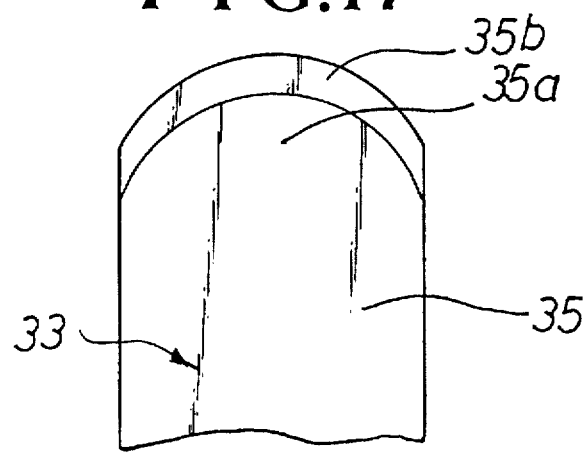
FIG. 17 is an enlarged plan view of the blade showing a modification of the ophthalmologic knife of the third embodiment.

FIG. 17 is an enlarged plan view of the blade showing a modification of the ophthalmologic knife of the third embodiment. In this modification, the tip portion 35a of the incision-forming portion 35 is not pointed but has an arcuate shape. Moreover, the cutting surface 35a is formed in an arcuate shape having a constant width. Except the blade, this ophthalmologic knife has the same structure as that of the ophthalmologic knife according to the first embodiment, and provides effects similar to those provided by the first embodiment.

In the above-describe embodiments, the blade has an arcuate cross section over the entire length of the blade. However, the blade may have a cylindrical cross section at the base portion thereof while having an arcuate or inverted-V-shaped cross section only at the incision-forming portion so as to provide a three-dimensional non-planar shape. However, it is essential that at least the portion of the blade which is inserted into the eyeball have a non-planar shape.

The non-planar shape is not limited to an upwardly curved arcuate shape and an inverted-V shape. The non-planar shape may be a downwardly curved arcuate shape, a V shape, a semielliptic shape, an isosceles trapezoidal shape which has rounded corners and one of whose longer sides is opened, an inverted-U shape, or a U shape.

The shape of the base portion of the blade, means for fixing the base portion of the blade to the tip of the handle, the shape and material of the handle may be changed to conventionally known shapes, means and materials.

The incision-forming portion of the blade may be modified so as to increase its width at the side adjacent to the base portion. Also, the planar shape of the cutting surface may be changed, and the cutting surface may be formed on each of the front and back faces of the blade.

Moreover, the portion in which a three-dimensional incision having an arcuate cross section or the like is formed by the incision-forming portion of the blade is not limited to the cornea. The ophthalmologic knifes according to the present invention can be used to from an incision such that it extends from the sclera to the cornea.

Obviously, numerous modifications and variations of the present invention are possible in light of the above teachings. It is therefore to be understood that within the scope of the appended claims, the present invention may be practiced otherwise than as specifically described herein.

What is claimed is:

1. An ophthalmologic knife comprising:
a handle; and
a blade having at least two faces, a base portion fixed to a tip of said handle and an incision-forming portion which is extended from said base portion,
wherein the blade or at least part of said incision-forming portion which is inserted into an eyeball has a non-planar cross section along a plane substantially perpendicular to said incision-forming portion, said non-planar cross section having a substantially smaller radial dimension than that of the eyeball to provide a smooth insertion of a three-dimensional object into the eyeball through an incision made in the eyeball by said knife and to provide incision resistance to widening in a vertical direction when said three-dimensional object is inserted into said eyeball.

2. An ophthalmologic knife according to claim 1, wherein said non-planar cross section is an arcuate cross section.

3. An ophthalmologic knife according to claim 1, wherein said non-planar cross section is an inverted-V-shaped cross section.

4. An ophthalmologic knife according to claim 2, wherein said incision-forming portion has a pointed cutting surface.

5. An ophthalmologic knife according to claim 4, wherein said cutting surface is formed only on one face of said blade.

6. An ophthalmologic knife according to claim 5, wherein said incision forming portion has a pointed tip and wherein said cutting surface consists of a pair of cutting surfaces formed on opposite sides of the pointed tip of said incision forming portion.

7. An ophthalmologic knife according to claim 6, wherein each of said cutting surfaces has a straight shape along a plane substantially parallel to said blade.

8. An ophthalmologic knife according to claim 6, wherein each of said cutting surfaces has an outwardly curved shape with respect to said blade and along a plane substantially parallel to said blade.

9. An ophthalmologic knife according to claim 2, wherein said incision-forming portion has a rounded cutting surface.

10. An ophthalmologic knife according to claim 9, wherein said cutting surface is formed only on one face of said blade.

11. An ophthalmologic knife according to claim 1, wherein a portion of said incision-forming portion extending from the tip of a cutting surface to a position slightly closer to said base portion relative to a base end of said cutting surface is used as in insertion portion which is inserted into an eyeball.

* * * * *